United States Patent [19]

Ramos Lazcano et al.

[11] Patent Number: 5,270,177
[45] Date of Patent: Dec. 14, 1993

[54] METHOD AND APPARATUS FOR THE PRODUCTION OF GLUCOSE-FRUCTOSE SYRUPS FROM SUCROSE USING A RECOMBINANT YEAST STRAIN

[75] Inventors: Ruben Ramos Lazcano; Asterio Cruz Perez; Nancy Figueroa Baele, all of Havana, Cuba

[73] Assignee: Centro de Ingenieria Genetica y Biotecnologia, Havana, Cuba

[21] Appl. No.: 879,856

[22] Filed: May 6, 1992

[30] Foreign Application Priority Data

May 7, 1991 [CU] Cuba ......................................... 92/91

[51] Int. Cl.⁵ ...................... C12P 19/00; C12N 11/02; C13R 1/08
[52] U.S. Cl. ......................................... 435/72; 127/41; 435/177; 435/178; 435/182; 435/254.2
[58] Field of Search ................... 435/72, 94, 178, 177, 435/182, 255; 127/41

[56] References Cited

U.S. PATENT DOCUMENTS

| | | | |
|---|---|---|---|
| 4,350,765 | 9/1982 | Chibata | 435/161 |
| 4,525,457 | 6/1985 | Sakata | 435/178 |
| 4,543,332 | 9/1985 | Jao | 435/180 |
| 4,617,274 | 10/1986 | Wegner | 435/255 |
| 4,670,387 | 6/1987 | Bucke | 435/97 |
| 4,797,358 | 1/1989 | Motai | 435/176 |

FOREIGN PATENT DOCUMENTS 0438200 7/1991 European Pat. Off. .
2618161 1/1989 France .

*Primary Examiner*—Michael G. Wityshyn
*Assistant Examiner*—Ralph Gitomer
*Attorney, Agent, or Firm*—Peter L. Michaelson

[57] ABSTRACT

The invention relates to the field of nutrition and the sugar industry and presents a method and apparatus for producing glucose-fructose liquors on an industrial scale from sugar or liquors thereof. The invention uses reactors packed with a catalyst with high hydrolytic activity, and these are installed within a sugar refining factory or in an industry which dissolves it, such that glucose-fructose syrup is produced in a single operation by a continuous flow of the sugar liquor. High levels of hydrolysis may be attained by modification of the residence time. The process of hydrolysis of the sugar does not significantly alter the color of the solution. The product obtained on an industrial scale can be used both in the food industry and in the pharmaceutical industry.

7 Claims, 2 Drawing Sheets

METHOD AND APPARATUS FOR THE PRODUCTION OF GLUCOSE-FRUCTOSE SYRUPS FROM SUCROSE USING A RECOMBINANT YEAST STRAIN

The present invention relates to the field of nutrition and the sugar industry and, in particular, a method for the production of glucose-fructose liquors on an industrial scale from sugar or liquors thereof, as well as the industrial apparatus used. The invention consists of a technologically simple process and apparatus, designed therefor, which makes it possible to obtain, from glucose-fructose syrups sucrose. Such syrups are encountering increasing demand throughout the food industry.

The establishment and application of immobilisation of amylases and glucose isomerase for the production of high-fructose liquors from corn starch (HFCS) with concentrations of 42% and 55% has made great strides [Teague, J. R. and Arnold, E. C., Sugar, Aug. 18 (1983)]. The consumption of these syrups by soft drinks factories in the U.S.A. was approved in 1980 and, presently, more than 60% of the glucose-fructose syrups produced are consumed in the soft drinks industry, even occupying 100% of sweetener consumption [Wuilleumeier, S., Sugar, Oct. 15 (1985)]. Up to now, this is the only industrial technology which makes it possible to obtain glucose-fructose syrups on this scale.

The manufacture of HFCS requires three different enzymatic reactions. The first enzyme, alpha-amylase, is used to liquefy starch into a solution with a low content of glucose equivalent, allowing subsequent reactions which take place within the liquid phase and making it possible to use filtration or separation techniques to eliminate insoluble substances which would hinder some subsequent steps of the process. The syrup obtained in this way is composed of certain quantities of oligosaccharides which are hydrolyzed with amyloglucosidase in order to increase the glucose content to approximately 95%. This syrup of 95% glucose is subjected to various purifying treatments before introducing it into the process of isomerisation where the third enzyme, glucose isomerase, is used.

The 42% HFCS is obtained on isomerising the purified and decolorised glucose syrup (HGS) with the enzyme glucose isomerase, with which the glucose is partially converted to an isomer thereof which is fructose. The process is technically and economically attractive, up to a conversion level of 42%, at which the enzyme loses a large part of its activity. Thus is obtained the 42% or first-yield HFCS which contains 42% fructose, 50% glucose and 8% other sugars and is sold at a concentration around 75%. Its sweetening capacity on a dry basis is 90–100% of that of sucrose.

This process for obtaining glucose-fructose syrups is composed of industrial operations with several steps in which three different types of enzymes are used to transform the corn starch used as the raw material. The industrial process with this technology involves the construction of a large factory with specially designed equipment which ensures operations of enzymatic hydrolysis, evaporation, filtration and decoloration of the syrups, as well as the establishment of the auxiliary supplies of energy, water, etc. On the other hand, the use of corn starch as a substrate for obtaining fructose liquors, apart from the fact of working with dilute solutions, which entails high expenditure on evaporation, gives rise to the need to use three different types of enzymes for hydrolysis. Unfortunately, the extraction and purification process of which from the producer microorganisms, as well as immobilization thereof for use in industrial reactors, is highly complex and costly.

It is also known from the Spanish patent publication 2007527, granted to firm Roguette Freres, that it is possible to obtain high-fructose syrups from plant raw materials which previously contain inulin. However, in this method, it is necessary to work with plants of which the yield per hectare is lower than sugar cane and starts from a polysaccharide which is more difficult to process.

SUMMARY OF THE INVENTION

The present invention relates to a process for the production of glucose-fructose syrups from sucrose, using a recombinant yeast strain (deposited under number CBS 452.90 in the collection of the Centraalbureau voor Schimmel-Cultures, CBS, The Netherlands) in which the gene which codes for the synthesis of sucrose invertase has been cloned and which has the peculiarity that it retains the enzyme produced in the cell periplasm, which makes it a very attractive system for use thereof in industrial processes which require the use of biocatalysts with the immobilised microorganism (European Patent Application No. 438 200 A1). The use of this microorganism has made it possible to construct industrial installations which, by the high degree of hydrolytic activity of the biocatalyst, determine the high efficiency and economic feasibility of the proposed industrial process.

Production of the catalyst is carried out with a peristaltic pump from a cell suspension for which between 10 and 12 kg of sodium alginate are weighed out and dissolved in 490–530 liters of water. Between 8 and 12 kg of biomass of strain MSUC-2 and between 5 and 50 g of 13X molecular sieves, are added to said solution. The solution is subsequently suspended in between 4 and 6 $m^3$ of a $CaCl_2$ solution which contains between 50 and 56 kg/10 $m^3$. The whole suspension is allowed to drip using needles with a diameter of 1 mm by means of a peristaltic pump, using a purpose-built screen consisting of 360 needles set in a device which allows continuous flow of 100–120 l/hour of the cell suspension in sodium alginate, with which 270–290 l of the biocatalyst are obtained from 1 $m^3$ of the suspension. The catalyst obtained is kept in a sugar solution with a concentration of 60°–70° Brix which guarantees transport and storage for more than one year without appreciable loss of activity.

This process is characterized by the use of reactors which contain the biocatalyst, which consists of a microorganism immobilised in calcium alginate as a carrier. These reactors are installed within the sugar production factory itself or in some other factory where sugar is dissolved for use thereof. Production of the glucose-fructose syrups obtained in a system of flow reactors is carried out continuously, in a single operation, adjusting the residence time and hence the level of sucrose inversion. Hydrolysis levels greater than 90% are obtained. In this way, a syrup is obtained with a colour the same as the input liquor and a sugar hydrolysis level depending on the flow rate which is established. Using 1 liter of catalyst, it is possible to hydrolyse, with approximately 90–95% inversion, 0.30–0.50 kg of sugar per hour, which is equivalent to 0.50–0.70 liters per hour of sucrose liquor of 60° Brix.

This technological process allows the production of glucose-fructose syrups with concentrations greater than 75% by a suitable combination of the reactors.

The system is continuous and can be automated. Hence the industrial apparatus necessary for the process of production of glucose-fructose syrups is very simple, the number of technological steps used for these purposes being reduced considerably.

DETAILED DESCRIPTION

Figure 1:
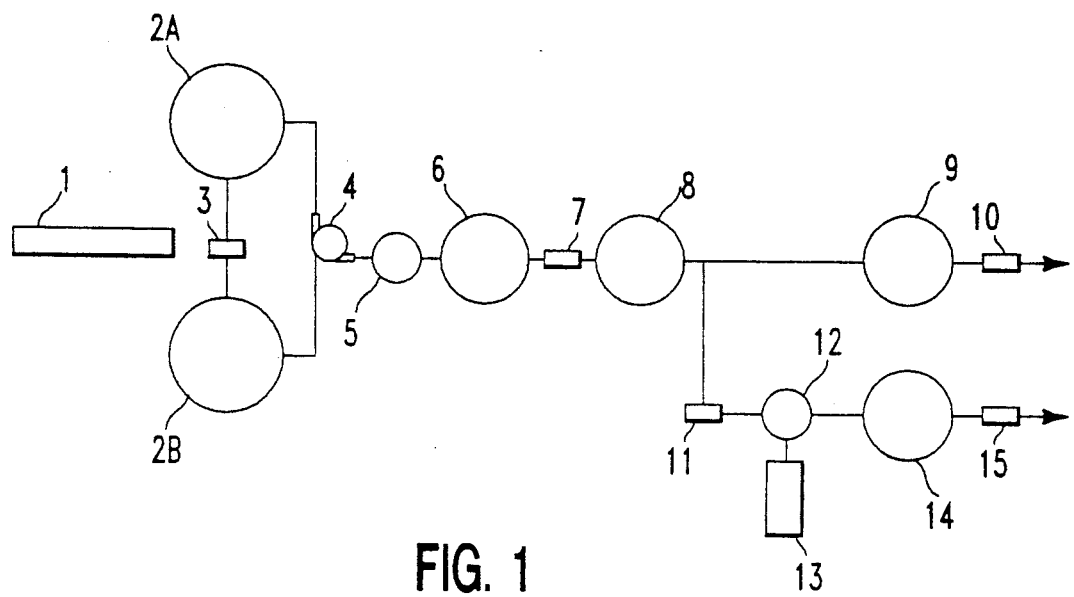
FIG. 1 depicts a process flow chart of glucose and fructose syrup production with dissolved sugar for a starting material as described in Example 3.
Figure 2:
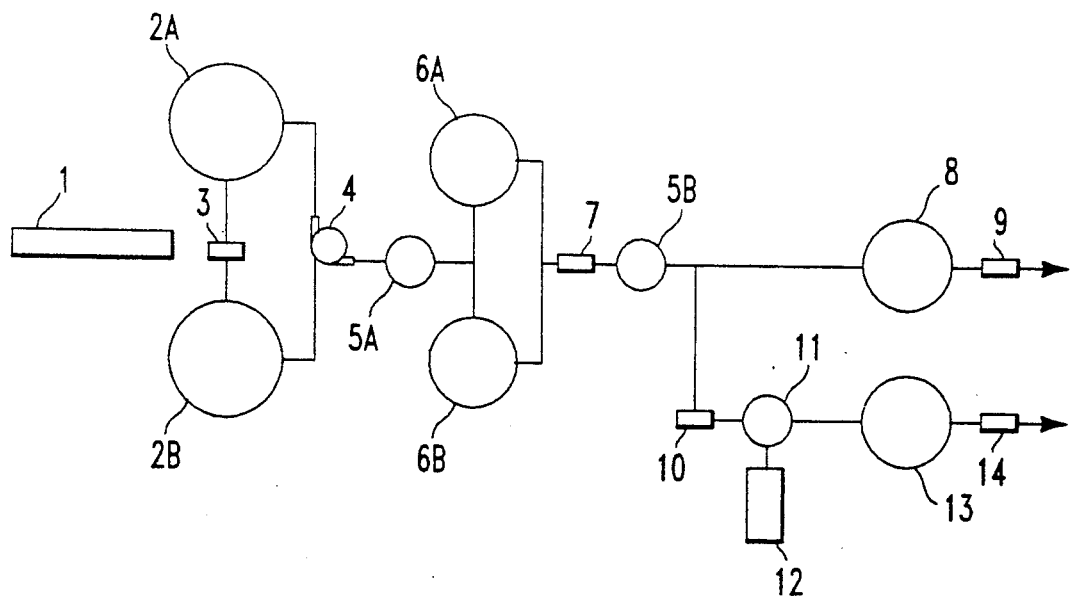
FIG. 2 depicts a process flow chart of glucose and fructose production with dissolved sugar for a starting material as described in Example 4.
Figure 3:
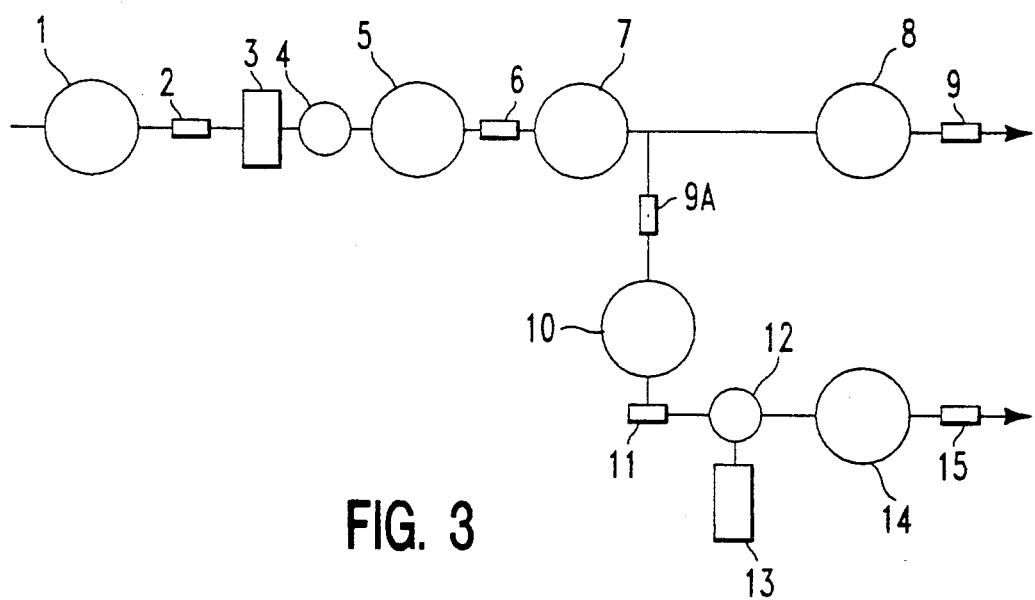
FIG. 3 depicts a process flow chart of glucose and fructose syrup production with sugar liquor as a starting material as described in Example 5.

The industrial apparatus for carrying out said technological process includes in the first instance a mat (1) for transport of the standard refined sugar [FIGS. 1 and 2], which goes to a system for supply of the bioreactor, which may be a sugar dissolving tank in the event of starting from dissolved sugar [FIGS. 1 and 2 (elements 2A and 2B)], or a storage tank when starting from sugar production liquors [FIG. 3 (1)].

In the event of starting from dissolved sugar, the dissolving tanks have a vertical agitator, a coil and a common recirculating pump [FIGS. 1 and 2 (3)]. The syrups are supplied by a pump [FIGS. 1 and 2 (4)] and pass to the columns packed with the biocatalyst [FIGS. 1 and 2 (5 and 5A)] and from there to the dissolving tanks [FIGS. 1 and 2 (6 and 6A-6B)].

As shown in FIG. 3, the invert syrup containing glucose-fructose of the dissolving tank (6) is delivered by the pump (7) to the evaporator (8) where it is concentrated to 75-78% and there it is delivered to the storage tank (9), which has a pump (10) for emptying it into the means of transport as a first variant. As a second variant, this concentrated fructose-glucose syrup is delivered by the pump (11) to the gas-liquid reactor (12), where the syrup reacts with ozone-enriched air from the ozoniser (13) to obtain a weak-colour syrup. From there, the syrup is delivered to the tank (14) from which the pump (15) transfers it to a transport.

In the event that the plant does not use the evaporator [FIG. 2], from the dissolving tanks (6A and 6B), the invert syrup is supplied by the pump (7) to the column (5B) packed with the biocatalyst. The invert syrup hydrolyzed to levels greater than 90% is delivered to the storage tank (8) which has a pump (9) for emptying it into a transport. With this system, higher concentrations of invert sugar of 75° Brix are obtained.

In the event, as shown in FIG. 3, that the initial raw material consists of decolorised and concentrated liquors of 60-65 degrees Brix from refineries, the liquors are admitted to a tank (1). From the tank, the liquors are pumped by the pump (2) through a heat exchanger (3) to the inversion column (4) packed with the biocatalyst. The invert syrup is poured into a receiving tank (5) from which it is pumped by the pump (6) to the evaporator (7) and concentrated to 75%. Subsequently, the concentrated syrup is delivered to the storage tank (8) which, in turn, has a pump (9) for emptying and transferring it. As another variant within this plant, the concentrated syrup is delivered by the pump (9A) to the gas-liquid reactor (10), where it reacts with the ozone-enriched air from the ozoniser (11), to obtain syrups of very weak colour. The latter are delivered to the tank (12), from which the pump (13) transfers them to the means of transport.

Practical Examples

EXAMPLE 1

For immobilisation of the microorganism, 10 kg of sodium alginate (BDH) for commercial use which is rich in glucuronic acid were weighed out, which was dissolved with agitation in 500 l of water. In this same solution were suspended 10 kg of biomass of strain MSUC-2 grown under the conditions described in the previous example, and 50 g of 13X molecular sieves (zeolite). 55.5 kg of $CaCl_2$ were weighed out and dissolved in 10 $m^3$ of water. Once the above conditions were prepared, the process of dripping the sodium alginate solution with the suspended microorganisms over 5 $m^3$ of $CaCl_2$ solution was performed. Dripping was obtained by means of a specially built device which has a large number of needles with a diameter of 1 mm and which, with a peristaltic pump, allows a flow rate of 200 l/hour. The gel obtained continued to be agitated for 2 hours and then it was decanted. 5 $m^3$ of the calcium chloride solution were added, to thin gel continuing agitation for another 12 hours, at the end of which the gel was rinsed with water. The approximate volume of alginate beads obtained is approximately 350 l. This operation was repeated until achieving a volume of 3.3 $m^3$ of biocatalyst.

EXAMPLE 2

For the purpose of preparing an industrial column for the hydrolysis of sucrose with the immobilised microorganism, first the biocatalyst obtained was characterised and the values of $W_{max}$ and $K_m$ of the Michaelis-Menten equation were specified, and using these laboratory values calculations were made for an industrial plant. On the basis of the values of $W_{max}$ and $K_m$ obtained for the optimum cell-alginate charge, calculations were made for a plant with a total biocatalyst volume of 3.3 $m^3$, which was used to charge six bioreactors of 540 l each in the form of columns 3 m high with a diameter of 0.5 m. For calculation, there was taken into consideration the expression of the dependence of residence time of the concentration on the substrate concentration, which is equal to:

$$t = \int_S^{S_0} dS/W \tag{1}$$

t is residence time,
$S_0$ is substrate concentration at the reactor input,
S is substrate concentration at the reactor output,
W is velocity of the reaction.

This equation is solved considering that the Michaelis-Menten expression equal to:

$$W = W_{max}[S]/K_m + [S] \tag{2}$$

where
$W_{max}$ is maximum velocity of the reaction,
$K_m$ is the Michaelis-Menten constant
Substituting (2) in equation (1), the value of the residence time is obtained as a function of the substrate concentrations at the input ($S_0$) and output ($S$) of the reactor, equal to:

$$T = K_m/W_{max} + \ln(S_0/S) + (S_0 - S)/W_{max} \qquad (3)$$

Given that:

$$F = V/T \qquad (4)$$

where
F is the input flow rate of the substrate,
V is the effective volume of the reactor,
substituting in (3), there is obtained:

$$V = F(W_{max}/K_m) + \ln(S_0 S) + (S_0/S)/W_{max} \qquad (3).$$

In order to be able to use this expression, the values of $W_{max}$ and $K_m$ calculated in the laboratory reactor are substituted, and the flow rate and concentration of sucrose at the column input, which is equal to $S_0$, are fixed. The sucrose output concentration which is equal to S is determined experimentally, and as a result the value of V is obtained, which is the effective volume of the reactor.

EXAMPLE 3

A plant is described for producing glucose and fructose syrups of weak colour from refined sugar, with a capacity of 1 ton of solids an hour. Standard refined sugar with a minimum polarisation of 99.8%, 100 colour units, 0.05% ash and 20 ppms maximum is used as the raw material. The finished product is a glucose and fructose syrup of 75° Brix, with 75% inversion and with a colour and ash content similar to those of the input sugar.

The technology consists of a series of operations which are the following. The refined sugar is poured from the bag onto the mat (1) [FIG. 1] which carries it to the dissolvers (2A and 2B) of 3 m³ each. The dissolvers have a vertical agitator, a coil and a common recirculating pump (3). Their capacity makes it possible to operate the system continuously for 2 hours each. Dissolution is carried out with condensed hot water to a concentration of 60%. The dissolvers have indicators of level, concentration and temperature, as well as a system for automatic regulation of the latter to 45° C.

The syrup of 60% and 45° C. is supplied by the pump (4) to the 3 m³ column (5) packed with the biocatalyst. Next the invert glucose and fructose syrup of the tank (6) is delivered by the pump (7) to the evaporator (8) where it is concentrated to 75% and delivered to the 60 m³ storage tank (9). The latter has the pump (10) for emptying it into the means of transport.

There is the option of delivering the concentrated glucose and fructose syrup by the pump (11) to the gas-liquid reactor (12) where it interacts with ozone-enriched air from the ozoniser (13) to obtain syrups with a very weak colour. These are delivered to the tank (14) with a capacity of 60 m³ from which the pump (15) transfers them to the means of transport.

All the equipment and devices used are made of coated steel, stainless steel or food-grade plastics.

The plant requires a single operator. The operation of valves and motors is performed from a distance by means of a central panel.

The plant is located in a covered area of about 40 m² and 6 meters high, depending on the local conditions.

EXAMPLE 4

A plant is described for producing glucose and fructose syrups of weak colour from refined sugar with a capacity of 1 ton of solids an hour. Standard refined sugar with a minimum polarisation of 99.8%, 100 colour units, 0.05% ash and 20 ppms maximum is used as the raw material. The finished product is a glucose and fructose syrup of 75° Brix, with 75% inversion and with a colour and ash content similar to those of the input sugar.

The technology consists of the following series of operations. The refined sugar is poured from the bag onto the mat (1) [FIG. 2] which carries it to the dissolvers (2A and 2B) of 3 m³ each. The dissolvers have a vertical agitator, a coil and a common recirculating pump (3). Their capacity makes it possible to operate the system continuously for 2 hours each. Dissolution is carried out with condensed hot water to a concentration of 60%. The dissolvers have indicators of level, concentration and temperature, as well as a system for automatic regulation of the latter to 45° C.

The syrup of 60% and 45° C. is supplied by the pump (4) to the 1.5 m³ column (5A) packed with the biocatalyst. Next, the invert glucose and fructose syrup is delivered alternately to the dissolving tanks (6A and 6B) where an additional quantity of sucrose is dissolved such that a concentration of 75° Brix is attained. The syrup of 75% and 45° C. is supplied by the pump (7) to the column (5B) with a volume similar to the first one, packed with the biocatalyst. The syrup of higher concentration is hydrolyzed to levels greater than 90%. Finally it is delivered to the 60 m³ storage tank, (8). The latter has the pump (9) for emptying the fluid into a transport. With this system, greater concentrations of invert sugar of 75° Brix are obtained without the need for evaporation.

There is the option of delivering the concentrated glucose and fructose syrup by the pump (10) to the gas-liquid reactor (11) where the syrup interacts with ozone-enriched air from the ozoniser (12) to obtain syrups with a very weak colour. These are delivered to the tank (13) with a capacity of 60 m³ from which the pump (14) transfer them to a transport.

All the equipment and devices used are made of coated steel, stainless steel or food-grade plastics.

The plant requires a single operator. The operation of valves and motors is performed from a distance by means of a central panel.

The plant is located in a covered area of about 40 m² and 6 meters high, depending on the local conditions.

EXAMPLE 5

A plant is described for producing glucose and fructose syrups of weak colour from decolorised and concentrated refinery liquor, with a capacity of 1 ton of solids an hour. Decolorised and concentrated refinery liquor of 60°-65° Brix with less than 150 colour units is used as the raw material. The finished product is a glucose and fructose syrup of 75° Brix, with 90% inversion and with a colour and ash content similar to those of the input liquor.

The technology consists of the following series of operations. The decolorised and concentrated refinery liquor [FIG. 3] is admitted to a 6 m³ tank (1) from which it is pumped by the pump (2) through a heat exchanger (3) to the inversion column (4) packed with the biocatalyst, in such a way that the liquor which supplies the column has a temperature of 45°±5° C., a pressure of 2-3 bar and a flow rate of 25 l/min. The column input line has measurement of flow rate, temperature and pressure.

The invert glucose and fructose syrup is poured into a receiving tank (5) from which it is pumped by the pump (6) to the evaporator (7) where it is concentrated to 75% and then, it is delivered to the 60 m³ storage tank (8) which, in turn, has a pump (9) for emptying and transferring it.

There is the option of delivering the concentrated glucose and fructose syrup by the pump (9A) to the gas-liquid reactor (10) where it interacts with ozone-enriched air from the ozoniser (11) to obtain syrups with a very weak colour. These are delivered to the tank (12) with a capacity of 60 m³ from which the pump (13) transfers them to a transport.

All the equipment and devices used are made of coated steel, stainless steel or food-grade plastics.

The plant requires a single operator, the valves and motors being operated from a distance by means of a central panel.

The plant is located in a covered area of about 40 m² and 6 meters high, depending on the local conditions.

EXAMPLE 6

In order to perform testing of the industrial plant to which the present invention relates, the columns described were installed in the refinery of Camilo Cienfuegos Sugar Factory situated in the town of Santa Cruz del Norte, in the province of Havana, Cuba. In this refinery, the decolorised and concentrated liquor of 65° Brix is hydrolyzed by acid hydrolysis with HCl to 63% inversion in order to be used in the production of beer in the city of Havana. The installation was arranged in parallel with the traditional stream of liquor, and calculated operating parameters were checked. According to expressions (3) and (4), for 63% hydrolysis of the sucrose present in the liquor, necessary to maintain a flow rate of 14.0 l/min should be maintained in order to obtain a residence time of 120 min. The annual production of this plant is 10,000 metric tons a year. On checking the sucrose concentration and the level of hydrolysis during a prolonged period of time, it was possible to demonstrate the theoretical value defined according to the mathematical expressions (3) and (4).

EXAMPLE 7

In order to obtain the calcium alginate beads, a device was constructed, consisting of a specially built screen which is composed of 360 needles with a diameter of 1 mm set in a sealed plastic casing which allows continuous flow of 100-120 l/hour of the cell suspension in sodium alginate, by means of which 270-290 l of the biocatalyst are obtained from 1 m³ of the suspension. The catalyst obtained is kept in a sugar solution with a concentration of 60°-70° Brix, which ensures transport and storage for more than one year without appreciable loss of activity.

Advantages of the proposed solution.

The plant of this system of inversion and evaporation in a sugar factory allows:

1) Up to 25% greater availability of sugar by
a) Elimination of losses in final molasses (syrup off).
b) Elimination of losses by driving in drying and cooling of the sugar.
c) Elimination of losses in storage and transport, as well as indeterminate losses.
d) Increase of solids dissolved by addition of a molecule of water to the sucrose, as well as by greater sweetening capacity of the syrups.

2) Up to 75% less energy consumption by:
a) Elimination of use of steam for evaporation in boilers of the liquors and molasses, both in the whole of refining and partially in the production of raw material by reprocessing of molasses, as well as in drying and cooling of the sugar.
b) Elimination of all centrifuges in the process of production of refined sugar and some of them in the raw material process by elimination of waste molasses. Reduction of pumps, movement of equipment and conductors.
c) Elimination of electrical peaks by not using centrifuges.
d) Substantial reduction of the refinery equipment reduces the costs of investment, as well as the costs of industrial production by reduction of energy consumption and greater availability of sugar.

3) Additionally, the use of this production process eliminates the use of bags for packing, replacing them with tanks, avoids reprocessing in packing, and releases areas, equipment and personnel, the operations being performed by the operation of pumps. The reduction in the number of industrial operations substantially reduces labour.

We claim:

1. Method for producing a fructose containing solution from a sucrose containing solution, comprising passing a sucrose containing solution through a bioreactor which contains a biocatalyst that comprises Pichia pastoris strain MSUC-2, deposited under number CBS 452.90 in the collection of the Centraalbureau voor Schimmel-Cultures, CBS, The Netherlands, an immobilized microorganism which is a producer of sucrose invertase, and recovering a fructose containing solution produced in said bioreactor.

2. Method according to claim 1 for the production on an industrial scale of glucose-frutose syrups from sucrose which starts with sucrose in solution in order to obtain syrups rich in fructose, comprising the operations of immobilising said microorganism which is a producer of sucrose invertase with highly hydrolytic activity, using said microorganism as a biocatalyst in bioreactors which are installed within a factory where sucrose-rich liquors are produced, and obtaining inversion of the substrate in a single continuous step of flow of the sucrose liquors through said bioreactors.

3. Method according to claim 1, wherein calcium alginate and molecular sieves are used as carriers for immobilisation of said microorganis and further comprising, dripping the biocatalyst with a peristaltic pump, and preparing an aqueous solution of the immobilised biocatalyst using 10-12 kg of sodium alginate dissolved in 490-530 liters of water to which 8-12 kg of biomass of strain MSUC-2 and 5-50 g of 13X molecular sieves are added.

4. Method according to claim 3, wherein the aqueous solution prepared is suspended in 4-6 m³ of a CaCl$_2$ solution which contains between 50 and 56 kg of calcium chloride per 10 m³.

5. Method according to claim 4, wherein a peristaltic pump and a plurality of needles having a diameter of 0.5-1 mm are used to drip said aqueous sodium alginate solution containing suspended cells of Pichia pastoris strain MSUC-2 and suspended particles of molecular sieve 13X into said solution of calcium chloride at a continuous flow rate of 100–200 l/hour.

6. Method according to claim 1, wherein 0.5 l of biocatalyst is used per one $m^3$ of fructose containing solution produced.

7. Method according to claim 1, wherein said sucrose containing solution comprises a decolorised and concentrated sucrose liquor of 55°–65° Brix and at a temperature of 40°–50° C. and is passed through the bioreactor at a flow rate of 14–25 l/min with a residence time of 120–220 min.

* * * * *